United States Patent

Nguyen

[11] Patent Number: 4,546,641
[45] Date of Patent: Oct. 15, 1985

[54] DENSITOMETER

[75] Inventor: Van H. Nguyen, San Gabriel, Calif.

[73] Assignee: International Telephone & Telegraph Corp., New York, N.Y.

[21] Appl. No.: 542,836

[22] Filed: Oct. 17, 1983

[51] Int. Cl.⁴ ............................................. G01N 9/00
[52] U.S. Cl. ................................................. 73/32 A
[58] Field of Search ............................. 73/32 A, 32 R

[56] References Cited

U.S. PATENT DOCUMENTS

| | | | |
|---|---|---|---|
| 3,776,024 | 12/1973 | Schlatter | 73/32 A |
| 3,795,136 | 3/1974 | Schlatter | 73/32 A |
| 3,805,174 | 4/1974 | Schlatter | 328/261 |
| 3,842,655 | 10/1974 | Schlatter | 73/32 A |
| 3,878,374 | 4/1975 | Schlatter | 73/32 A |
| 3,883,811 | 5/1975 | Schlatter | 328/155 |
| 3,906,198 | 9/1975 | November | 73/32 A |
| 4,037,459 | 7/1977 | Schlatter | 73/32 A |
| 4,151,743 | 5/1979 | Ghahramani | 73/32 A |
| 4,274,016 | 6/1981 | Ghahramani | 307/270 |

Primary Examiner—Stewart J. Levy
Assistant Examiner—Hezron E. Williams
Attorney, Agent, or Firm—T. L. Peterson; E. C. Jason

[57] ABSTRACT

A vibration densitometer including a synchronous detector, a threshold detector, an integrator, an electromagnetic bridge driver, a piezoelectric crystal pick-off, a voltage controlled oscillator (VCO), a phase detector responsive to the crystal output and that of the VCO to control the VCO frequency and/or phase to provide an output signal of a frequency to energize the driver.

4 Claims, 14 Drawing Figures

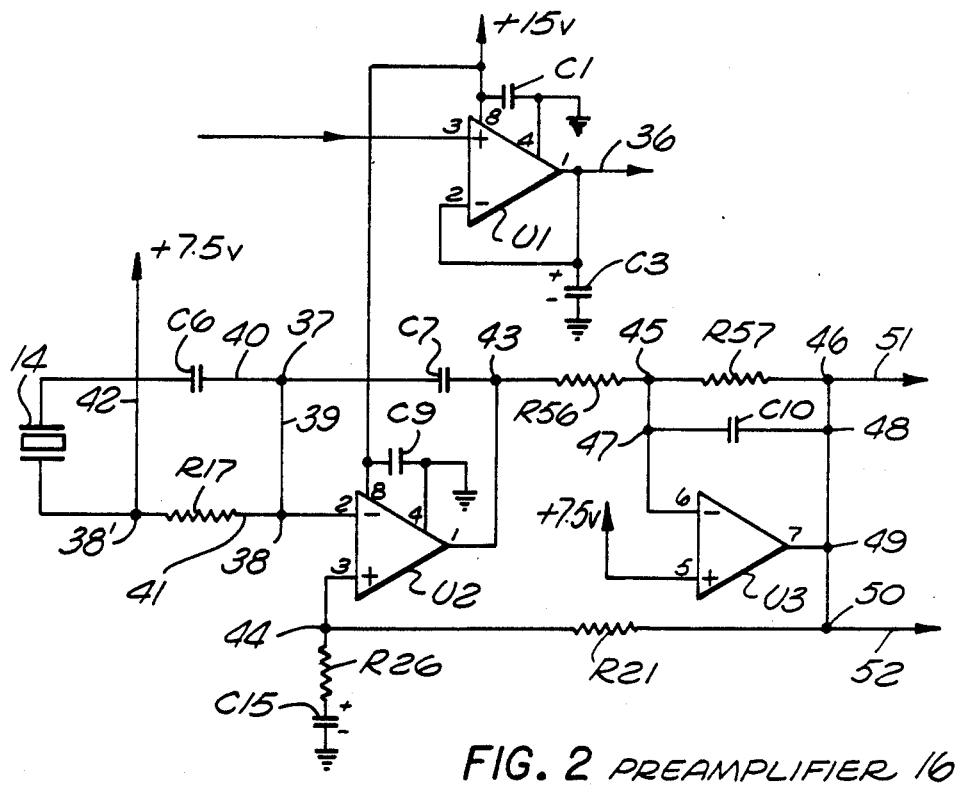
FIG. 2 PREAMPLIFIER 16
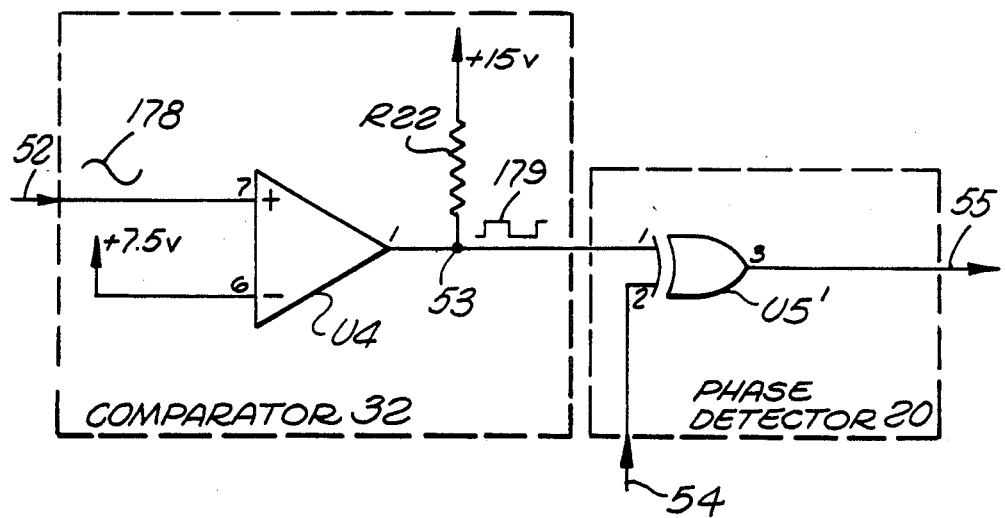
FIG. 3

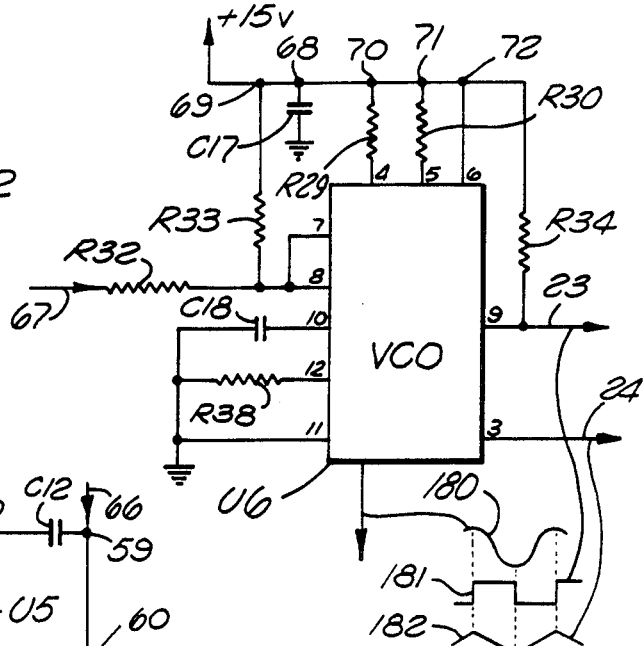

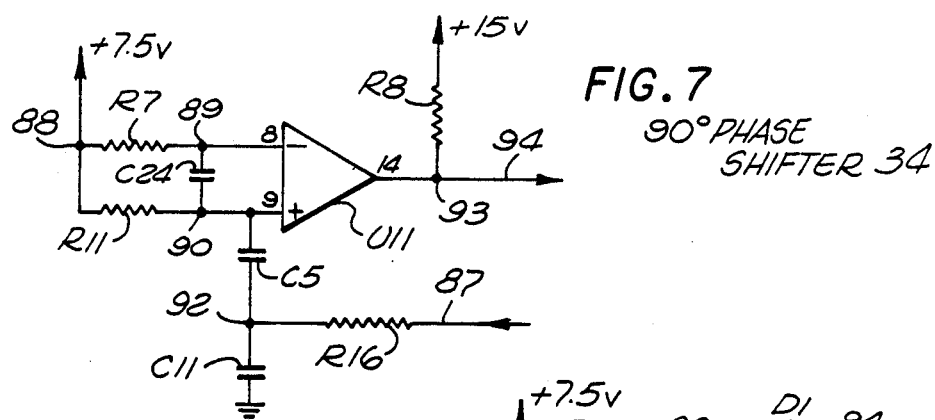
FIG. 7 90° PHASE SHIFTER 34
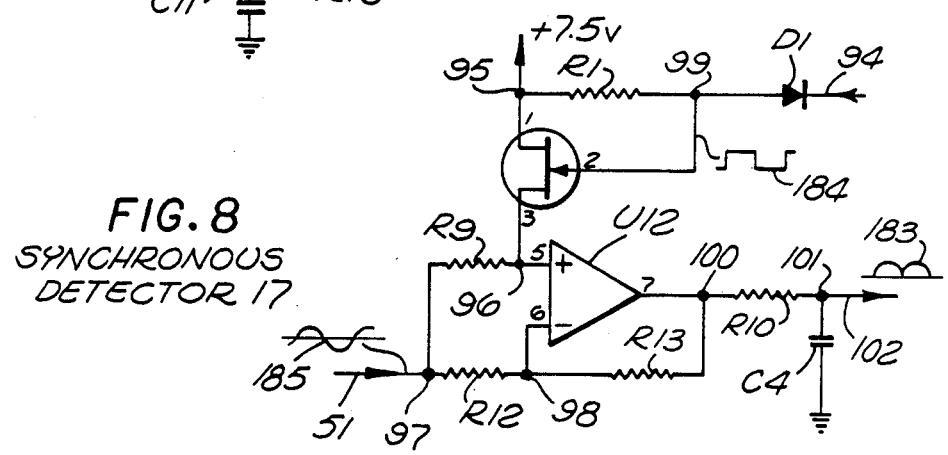
FIG. 8 SYNCHRONOUS DETECTOR 17
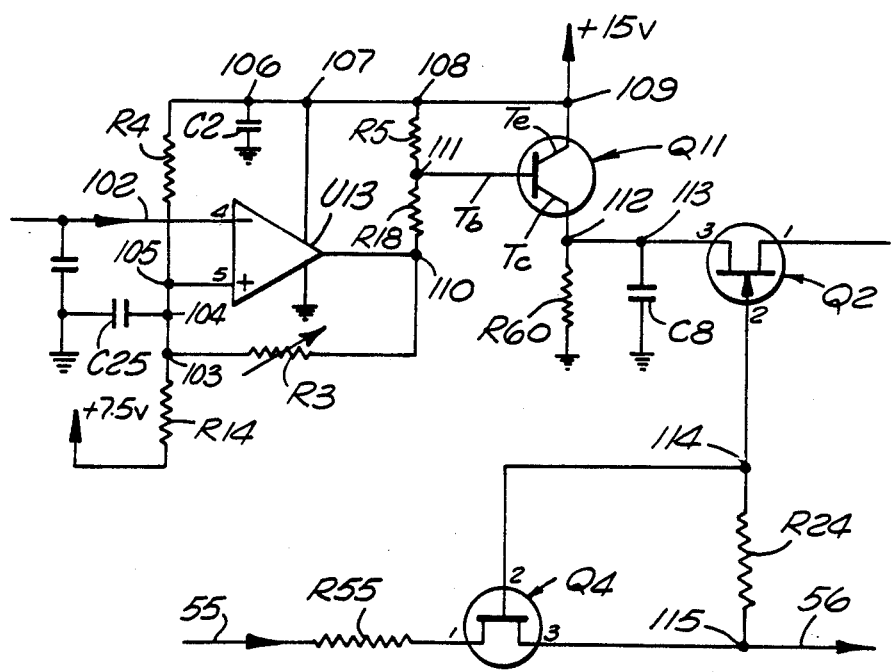
FIG. 9 THRESHOLD DETECTOR 18

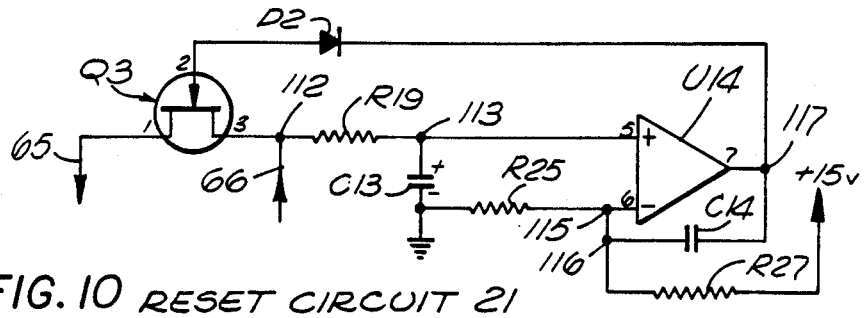
FIG. 10 RESET CIRCUIT 21
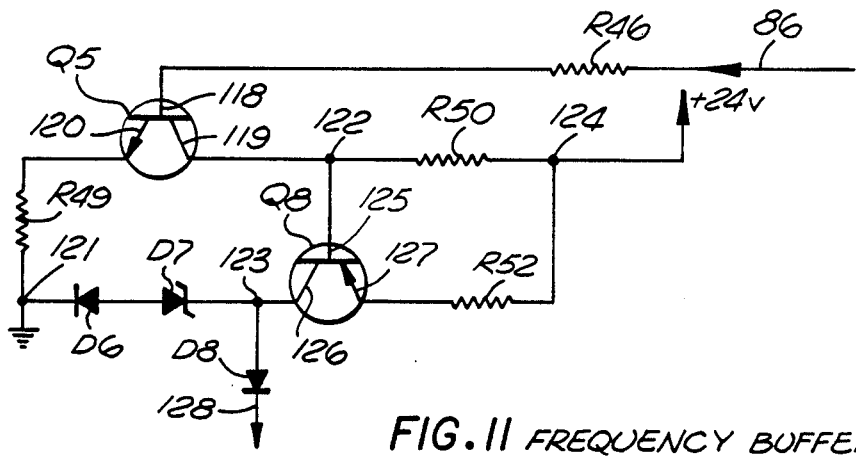
FIG. 11 FREQUENCY BUFFER 27
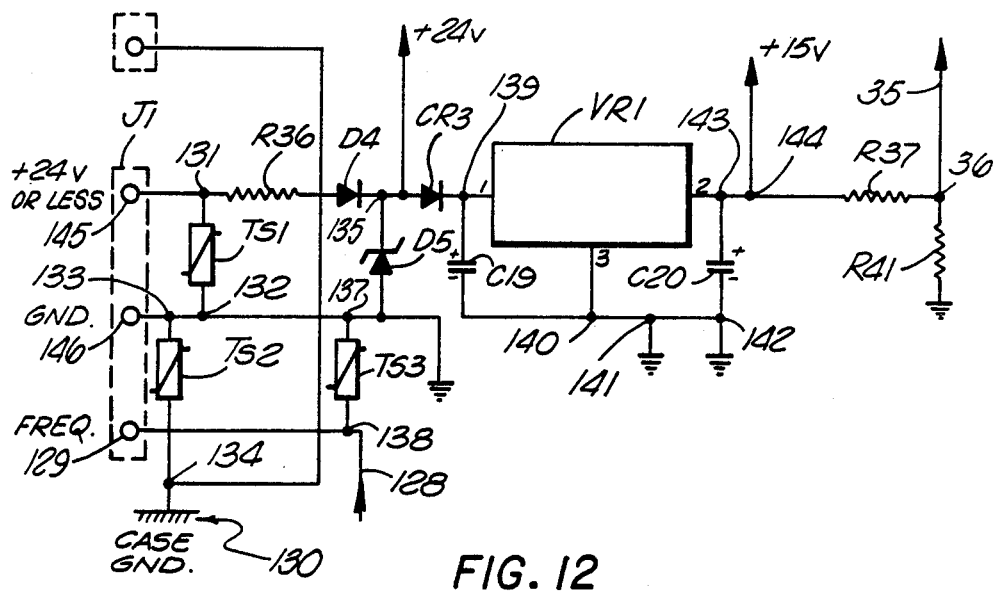
FIG. 12
REGULATOR CIRCUIT 29

FIG. 13 BRIDGE DRIVER 15

DENSITOMETER

BACKGROUND OF THE INVENTION

This invention relates to means for producing an electrical signal of a magnitude directly proportional to the density of a fluid, and more particularly to a vibration densitometer.

PRIOR ART STATEMENT

Prior art concerning vibration densitometers is somewhat extensive. This is especially true from the year 1971 to the present.

Pertinent patents of the prior art include the following.

The following patents disclose a synchronous detector for control of an output signal. However, these patents do not disclose a threshold detector actuable by a synchronous detector.

| U.S. PAT. NO. | ISSUE DATE |
|---|---|
| 3,878,374 | April 15, 1975 |
| 3,776,024 | December 4, 1973 |
| 3,795,136 | March 5, 1974 |
| 3,805,174 | April 16, 1974 |
| 3,842,655 | October 22, 1974 |
| 3,862,568 | January 28, 1975 |

The following patent discloses a voltage controlled oscillator (VCO) in a vibration densitometer circuit, but not connected directly from a preamplifier via a phase detector and integrator.

| U.S. PAT. NO. | ISSUE DATE |
|---|---|
| 3,883,811 | May 13, 1975 |

Each of the following patents discloses a threshold detector to operate a sweep oscillator input and a phase locked loop (with VCO) input:

| U.S. PAT. NO. | ISSUE DATE |
|---|---|
| 4,037,459 | July 26, 1977 |
| 4,274,016 | June 16, 1981 |
| 4,151,783 | May 1, 1979 |
| 4,215,566 | August 5, 1980 |

Vibration densitometers are also disclosed in the following:

| U.S. PAT. NO. | ISSUE DATE |
|---|---|
| 3,677,067 | July 18, 1972 |
| 3,706,220 | December 19, 1972 |
| 3,738,155 | June 12, 1973 |
| 3,741,000 | June 26, 1973 |

SUMMARY OF THE INVENTION

In accordance with one aspect of the present invention, there is provided a densitometer in which a preamplifier is directly connected to a voltage controlled oscillator (VCO) via a phase detector and threshold detector, the phase detector having an additional input which is a function of the VCO output.

In accordance with another aspect of the present invention, a synchronous detector operates the threshold detector.

BRIEF DESCRIPTION OF THE DRAWINGS

In the accompanying drawings which illustrate exemplary embodiments of the present invention:

FIG. 2 is a schematic diagram of a preamplifer;

FIG. 3 is a schematic diagram of a comparator and a phase detector;

FIG. 4 is a schematic diagram of an integrator;

FIG. 5 is a schematic diagram of a voltage controlled oscillator;

FIG. 6 is a schematic diagram of a phase adjustment circuit and an inverter;

FIG. 7 is a schematic diagram of a 90° phase shifter;

FIG. 8 is a schematic diagram of a synchronous detector;

FIG. 9 is a schematic diagram of a sweep threshold detector;

FIG. 10 is a schematic diagram of a reset circuit;

FIG. 11 is a schematic diagram of a frequency buffer;

FIG. 12 is a schematic diagram of a regulator circuit;

DESCRIPTION OF THE PREFERRED EMBODIMENT

Figure 1:
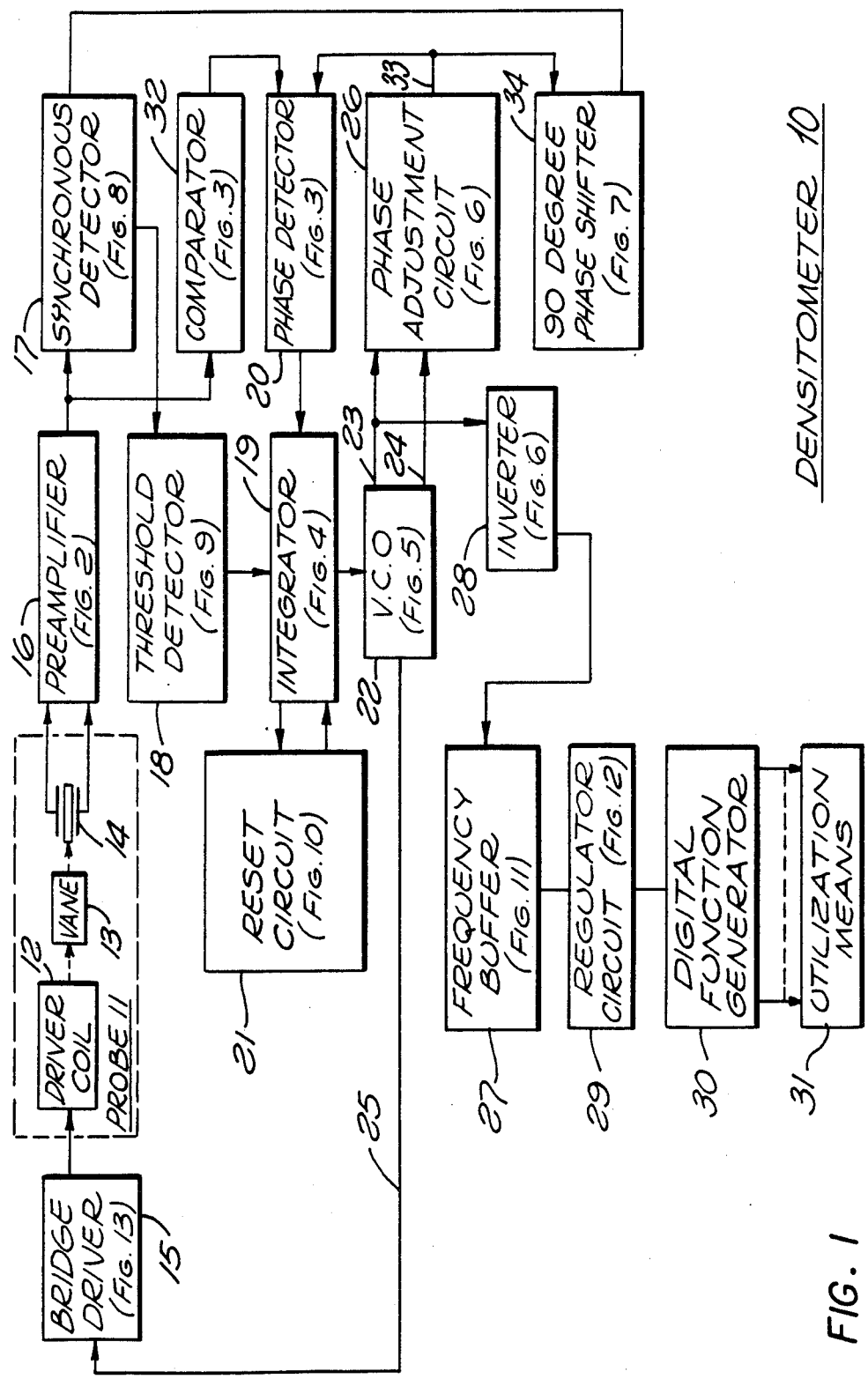
FIG. 1 is a block diagram of a densitometer.

A densitometer 10 is shown in FIG. 1 having a probe 11. Probe 11 may be entirely conventional. Probe 11 may have a driver coil 12, a vane 13 and a piezoelectric crystal 14. The input to the driver coil 12 is supplied through a bridge driver 15 also shown in FIG. 13.

The output of crystal 14 is impressed upon a preamplifier 16 that is connected to a synchronous detector 17. Preamplifier 16 and synchronous detector 17 are respectively shown also in FIGS. 2 and 8.

The output of synchronous detector 17 is connected to a threshold detector 18 also shown in FIG. 9.

The output of threshold detector 18 is impressed upon an integrator 18. Integrator 19 also receives inputs from a phase detector 20 and a reset circuit 21 shown in FIGS. 9 and 10.

In FIG. 1, the output of integrator 19, also shown in FIG. 4, is impressed upon a voltage controlled oscillator (VCO) 22. VCO 22 has outputs 23, 24 and 25. Outputs 23 and 24 are connected to a phase adjustment circuit 26, also shown in FIG. 6. VCO output lead 25 is connected to bridge driver 15, and lead 23 is connected to a frequency buffer 27 via an inverter 28. Inverter 28 and frequency buffer 27 are respectively shown also in FIGS. 6 and 11.

The input supply voltage is current limited and supplies power to the bridge driver 15, frequency buffer 27 and regulator circuit 29. Output of regulator circuit 29 supplies power to the rest of the circuit. The regulator circuit 29 has over-voltage, over-current protection and reverse and transient voltage protection. The frequency buffer 27 has reverse voltage and transient voltage (lightning or surge) protection. Digital function generator 30 and utilization means 31 may be powered from the same supply voltage or from another supply voltage.

If desired, the density of a fluid may be shown on an indicator in utilization means 31 in a known way. A comparator 32 is connected from the output of preamplifier 16 to phase detector 20. Phase adjustment circuit 26 has a common output 33 which is impressed upon phase detector 20 and a 90° phase shifter 34. The output of 90° phase shifter 34 is impressed upon synchronous detector 17.

Probe 11, comparator 32, VCO 22, frequency buffer 27, regulator circuit 29, digital function generator 30 and utilization means 31 may be entirely conventional. Probe 11 may be of the type disclosed in U.S. Pat. No. 4,194,385 issued Mar. 25, 1980. Preamplifier 16 shown in FIG. 2 has three differential amplifiers U1, U2 and U3. Amplifier U1 has an noninverting input at terminal 3 which is connected from a lead 35. Lead 35 is connected from a junction 36 in regulator circuit 29 shown in FIG. 12.

Amplifier U1 has terminals 4 and 8 connected across a compacitor C1, terminal 4 being connected to ground. Terminal 8 is connected to a potential of +15V. Amplifier U1 has an output lead 36. This output lead is connected to a positive plate of a capacitor C3. The same is true of the inverting input at terminal 2 of amplifier U1. Lead 36 supplies +7.5 volts to the densitometer circuits of FIG. 1.

Amplifier U2 is connected in the same manner as amplifier U1 except that noninverting terminal 3 is connected to ground successively through a resistor R26 and a capacitor C15. Junctions 37 and 38 are formed at the intersections of a crosswire 39 and input leads 40 and 41. A capacitor C6 is connected from crystal 14 to junction 37. A resistor R17 is connected from junction 38' to junction 38. Crystal 14 is connected from capacitor C6 to junction 38'. A lead 42 is connected from junction 38' to +7.5 volts. Junctions are also provided at 43, 44, 45, 46, 47, 48, 49 and 50. A capacitor C7 is connected between junctions 37 and 43. The output of amplifier U2 is connected to junctions 43. A resistor R21 is connected from junction 44 to junction 50. A resistor R56 is connected between junctions 43 and 45. A resistor R57 is connected between junctions 45 and 46. A capacitor C10 is connected between junctions 47 and 48.

Junctions 45 and 47 are connected to the inverting input of amplifier U3. Junctions 46, 48, 49 and 50 are connected together. The output of amplifier U3 is connected to junction 49. The noninverting input of amplifier U3 is connected to potential +7.5 volts. Preamplifier 16 has output leads 51 and 52 connected respectively from junctions 46 and 50. Lead 51 in preamplifier 16 shown in FIG. 2 extends into synchronous detector 17 shown in FIG. 8. Lead 52 in FIG. 2 also extends to comparator in FIG. 3.

In FIG. 3, comparator 32, actually a squarer, includes a differential comparator U4 having an inverting input connected from +7.5 volts and a noninverting input connected from lead 52. The output of comparator U4 is connected to a junction 53 which, in turn, is connected to an exclusive OR (EX-OR) gate U5 shown in phase detector 20. A resistor R22 is connected from junction 53 to +15 volts. EX-OR gate U5' also has an input from a lead 54 at the output of phase adjustment circuit 26 shown in FIG. 6. EX-OR gate U5' has an output lead 55 connected to a resistor 55 shown in threshold detector 18 in FIG. 9.

Threshold detector 18 has an output lead 56 in FIG. 9 which is connected to the inverting input 2 of differential amplifier U5 in the integrator 19 of FIG. 4. Integrator 19 is provided with junctions at 57, 58, 59, 60, 61, 62, 63 and 64. Junction 57 is connected to +15 volts. Terminals 4 and 8 of a differential amplifier U5 are connected across a capacitor C16, junction 62 being grounded and being connected to terminal 4. Junction 61 is connected from terminal 8. Junctions 57 and 61 are connected together. Amplifier U5 has an inverting input connected from junction 64. Junctions 58 and 64 are connected together. Integrator 19 has reset leads 65 and 66 connected to junctions 58 and 59, respectively. A resistor R20 and a capacitor C12 are connected in succession from junction 58 to junction 59. Junctions 59 and 60 are connected together. The output of amplifier U5 is connected to junction 60. An output lead is provided at 67 connected from junction 60. A resistor R28 is connected from junction 57 to junction 63. A resistor R31 is connected from junction 63 to ground.

Output lead 67 of integrator 19 shown in FIG. 4 is connected to a resistor R32 in FIG. 5. A voltage controlled oscillator (VCO) U6 in FIG. 5 may be entirely conventional and may be of the type known as an ICL 8038. The terminal connections thereof are also conventional. Terminal 11 is connected to ground. Terminal 12 is connected to ground through a resistor R38. Terminal 10 is connected to ground through capacitor C18. Terminals 7 and 8 are connected together. A resistor R33 is connected from a junction 69 at +15 volts to terminal 8. Resistor R32 is connected from lead 67 to terminal 8. A capacitor C17 is connected from a junction 68 to ground, junction 68 being connected to junctions 69, 70, 71 and 72. A resistor R29 is connected from junction 70 to terminal 4. A resistor R30 is connected from junction 71 to terminal 5. Terminal 6 is connected to junction 72. A resistor R34 is connected from junction 72 to first output lead 23. Terminal 9 is connected to output lead 23. Terminal 3 is connected to another output lead 24. Still a third output lead 75 is connected from terminal 2.

Figure 13:
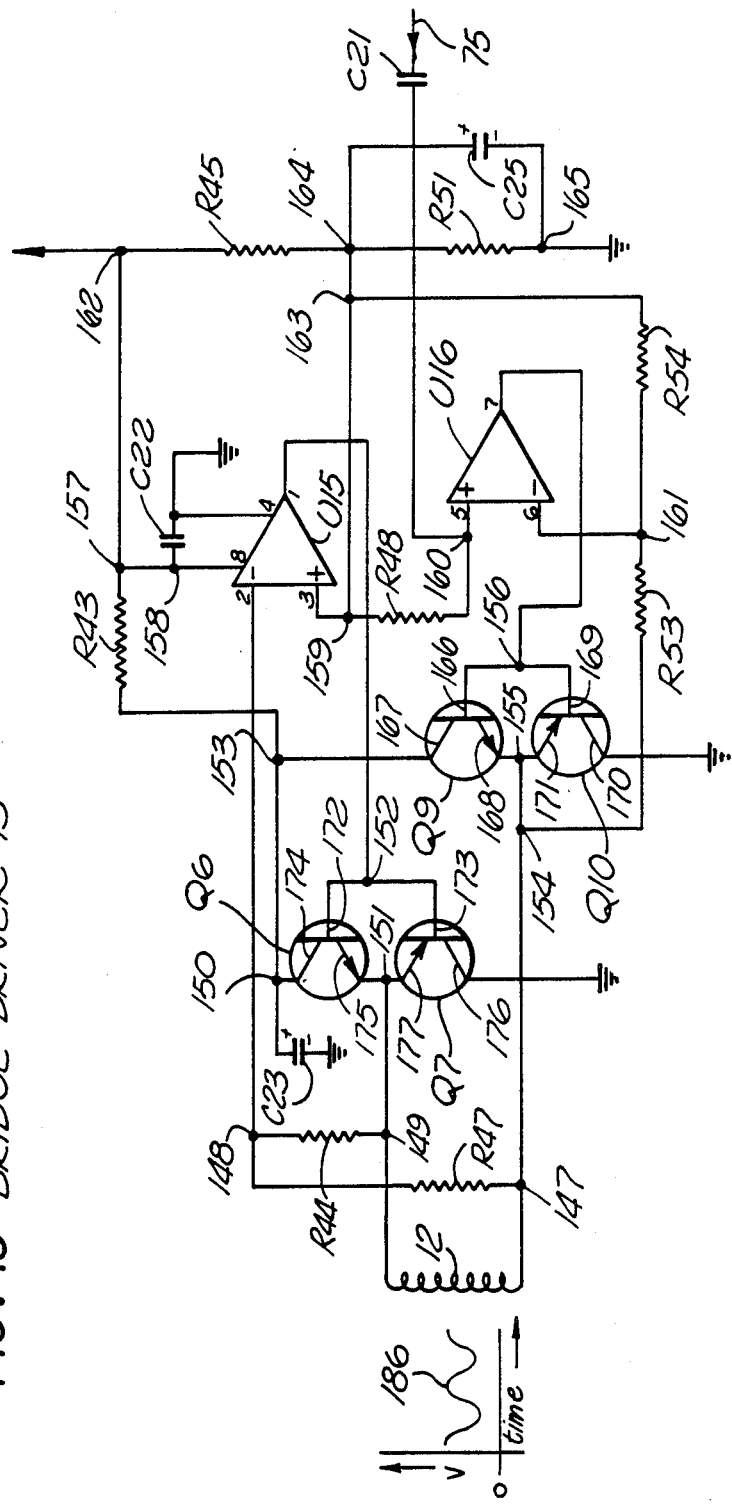
FIG. 13 is a schematic diagram of a bridge driver.

Lead 75 in FIG. 5 extends to bridge driver 15 shown in FIG. 13.

Leads 23 and 24 in FIG. 5 extend to phase adjustment circuit 26 shown in FIG. 6.

In FIG. 6, junctions are provided at 76, 77, 78, 79, 80, 81, 82, 83 and 85.

In FIG. 6, junction 85 is connected to terminal 6 of EX-OR gate U7, and to potential +15 volts. A comparator U8 is also provided in phase adjustment circuit 26 of FIG. 6. Comparator U8 has an output terminal 13 connected to junction 79. Junction 78 is connected to the noninverting input at terminal 11 of comparator U8. A resistor R42 is connected between junctions 79 and 85. Junction 79 is also connected to terminal 8 of another exclusive OR gate U9. Terminal 9 of EX-OR gate U9 is connected to ground through junction 80. Terminal 7 is also connected to junction 80. The output terminal 10 of EX-OR U9 is connected to junction 81.

A resistor R59 is connected between junctions 82 and 83. Junction 83, junction 81 and lead 54 are connected together.

Lead 24 is connected to the inverting input on terminal 10 of comparator U8. An EX-OR gate U7 is provided having a terminal 5 connected from junction 76. Lead 23 is connected to terminal 5 of EX-OR gate U7 via junction 76, and via the same junction to a terminal 13 of an exclusive OR gate U10 in inverter 28.

An EX-OR gate U7 is provided having an output terminal 4 connected to junction 78 through a resistor R39. A potentiometer R40 is connected between junction 78 and junction 82. EX-OR gate U10 has an output lead 86. An output lead is also provided from phase adjustment circuit 26 in FIG. 6 at 87. Lead 86 in FIG. 6 is an input lead to the frequency buffer 27 of FIG. 11. Lead 87 in FIG. 6 is the same lead in the 90° phase shifter 34 of FIG. 7.

Output lead 54 shown in FIG. 6 is the same as input lead 54 to phase detector 20 shown in FIG. 3.

Phase shifter 34 shown in FIG. 7 includes comparator U11. Phase shifter 34 has junctions 88, 89, 90, 91, 92 and 93. Junction 88 is connected to +7.5 volts. A resistor R7 is connected between junctions 88 and 89. A resistor R11 is connected between junctions 88 and 90. A capacitor C24 is connected between junctions 89 and 90. Junction 89 is connected to the inverting input terminal 8 of comparator U11. Junction 91 is connected to the noninverting input terminal 9 of comparator U11. Junctions 90 and 91 are connected together. A capacitor C5 is connected between junctions 91 and 92. A resistor R16 is connected from lead 87 to junction 92. A capacitor C11 is connected from junction 92 to ground. The output terminal 14 of comparator U11 is connected to junction 93. A resistor R8 is connected from +15 volts to junction 93. The output lead of phase shifter 34 is indicated at 94. Lead 94 is an input lead of synchronous detector 17 shown in FIG. 8.

As stated previously, input lead 51 in synchronous detector 17 of FIG. 8 arrives from preamplifier 16 in FIG. 2 to provide an input signal therefor. A square wave arrives on lead 94 from phase shifter 34 in FIG. 7. Synchronous detector 17 then has junctions 95, 96, 97, 98, 99, 100 and 101. Synchronous detector 17 has an output lead 102 which, in fact, is an input lead to threshold detector 18 shown in FIG. 9.

In the synchronous detector 17 of FIG. 8, a diode D1 is connected between junction 99 and input lead 94. A resistor R1 is connected between junctions 95 and 99. Junction 95 is maintained at a potential of +7.5 volts. A field effect transistor (FET) is provided having a gate terminal 2 connected from junction 99, a drain terminal 1 connected from junction 95, and a source terminal 3 connected to junction 96.

A resistor R9 is connected between junctions 96 and 97. A resistor R12 is connected between junctions 97 and 98. A resistor R13 is connected between junctions 98 and 100. The noninverting input terminal 5 of a differential amplifier U12 is connected from junction 96. The inverting input terminal 6 of amplifier U12 is connected from junction 98. The output terminal 7 of amplifier U12 is connected to junction 100. A resistor R10 is connected between junctions 100 and 101. A capacitor C4 is connected from junction 101 to ground. Output lead 102 is connected from junction 101.

In FIG. 9, threshold detector 18 includes junctions 103, 104, 105, 106, 107, 108, 109, 110, 111, 112, 113, 114 and 115. Junction 105 is connected to terminal 5 of a comparator U13. Terminal 5 of this comparator is the noninverting input thereof. The inverting input terminal 4 of comparator U13 is connected from lead 102.

Junctions 103, 104 and 105 are connected together. A capacitor C8 is connected between junction 113 and ground. A resistor R14 is connected between junction 103 and +7.5 volts. An adjustable feedback resistor R3 is connected between junctions 103 and 110. A resistor R4 is connected between junctions 105 and 106. A capacitor C2 is connected from junction 106 to ground. Junctions 106, 107, 108 and 109 are connected together and to +15 volts. A resistor R5 is connected between junctions 108 and 111. A resistor R18 is connected between junctions 110 and 111. The output of amplifier U13 is connected to junction 110.

A transistor Q11 has a collector $T_c$ connected to junction 112, an emitter $T_e$ connected to junction 109, and a base $T_b$ connected from junction 111. A resistor R60 is connected from junction 112 to ground.

A resistor R24 is connected between junctions 114 and 115. Junctions 112 and 113 are connected together. A FET Q4 is provided having a drain at terminal 1 connected from input lead 55 via a resistor R55, and a source terminal 3 connected to junction 115. Another FET Q2, acting as a diode, has a drain terminal 3 connected from junction 113, and a gate terminal 2 connected through resistor R24 to junction 115.

Leads 65 and 66 in the integrator 19 of FIG. 4 extend from the reset circuit 21 shown in FIG. 10. Reset circuit 21 contains a FET Q3 having a drain terminal 1 connected to lead 65, and a source terminal 3 connected to lead 66 via a junction 112. Reset circuit 21 has other junctions 113, 114, 115, 116 and 117. A resistor R19 is connected between junctions 112 and 113. Junction 113 is connected to terminal 5 at the noninverting input of a differential amplifier U14. A capacitor C13 is connected between junctions 113 and 114. Junction 114 is grounded. A resistor R25 is connected between junctions 114 and 115. Junction 115 is connected to terminal 6 of amplifier U14, the inverting input of amplifier U14.

Junctions 115 and 116 are connected together. A capacitor C14 is connected between junctions 116 and 117. The output terminal 7 of amplifier U14 is also connected to junction 117. A diode D2 is connected between the gate terminal 2 of FET Q3 to junction 117. A resistor R27 is connected from junction 116 to +15 volts.

In FIG. 11, frequency buffer 27 includes resistor R46 connected from lead 86 to the base 118 of an NPN type transistor Q5. Transistor Q5 has a collector 119 and an emitter 120.

In the frequency buffer 27 of FIG. 11, junctions 121, 122, 123 and 124 are provided. A resistor R49 is connected from emitter 120 to junction 121. Junction 121 is grounded. Collector 119 is connected from junction 122. A resistor R50 is connected between junctions 122 and 124. Junction 124 is connected to +24 volts. A PNP type transistor Q8 is also provided. Transistor Q8 has a base 125, a collector 126 and an emitter 127. A resistor R52 is connected between emitter 127 and junction 124. Base 125 is connected from junction 122. Collector 126 is connected from junction 123. A diode D8 is connected from junction 123 to an output lead 128. Diode D6 and zener D7 are connected between junctions 121 and 123.

Output lead 128 is connected to a terminal 129 shown in regulator circuit 29 in FIG. 12. Terminal 129 is connected to digital function generator 30 shown in FIG. 1.

In the regulator circuit 29 of FIG. 12, the case ground is indicated at 130. In FIG. 12, circuit components TS1, TS2 and TS3 are conventional and generally have the circuit characteristics of zener diodes. A zener diode D5 is, in fact, shown in FIG. 12. In FIG. 12, a 24 volt terminal is provided at 145 and a ground terminal is provided at 146. Component TS1 is connected between junctions 131 and 132. Junction 131 is connected from terminal 145. A resistor R36 and a diode D4 are connected in succession in that order from junction 131 to junction 135. Component TS2 is connected from junction 133 to junction 134. Junction 133 is connected from terminal 146. Junctions 132, 133, 136 and 137 are all connected together and connected to ground. Junction 134 is connected to case ground.

Component TS3 is connected between junctions 137 and 138. Junction 138 is connected from lead 128. Diode D5 is connected between junctions 135 and 136. A diode CR3 is connected between junctions 135 and 139. Junction 135 is connected to a potential of +24 volts. A capacitor C19 is connected between junctions 139 and 140. Junctions 140, 141 and 142 are all connected together and to ground. A capacitor C20 is connected between junctions 142 and 143. Junctions 143 and 144 are connected together. Junction 144 is +15 volts (output of regulator). A resistor R37 is connected between junctions 36 and 144. A resistor R41 is connected from junction 36 to ground. As stated previously, lead 35 is connected to preamplifier 16 as shown in FIG. 2. A component VR1 shown in FIG. 12 is a voltage regulator of a type 78M15. Regulator VR1 is entirely conventional. Regulator VR1 has terminals 1, 2 and 3 connected respectively to junctions 139, 143 and 140.

Bridge driver 15 is shown in FIG. 13. Bridge driver 15 may be entirely conventional, if desired. In FIG. 13, note that bridge driver 15 has input lead 75 connected from VCO 22 (FIG. 5). Further, bridge driver 15, or the drawing thereof shown in FIG. 13, includes coil 12 also shown in probe 11 in FIG. 1.

The bridge driver 15 shown in FIG. 13 includes junctions 147, 148, 149, 150, 151, 152, 153, 154, 155, 156, 157, 158, 159, 160, 161, 162, 163, 164 and 165. Junction 162 is maintained at a potential of +24 volts. Junctions 157 and 162 are connected together. A resistor R45 is connected between junctions 162 and 164. Junctions 159, 163 and 164 are connected together. A capacitor C25 is connected between junctions 164 and 165. The same is true of a resistor R51. Input lead 75 is connected to junction 160 via capacitor C21. Junction 160 is connected to the noninverting input of a differential amplifier U16 on terminal 5 thereof. The inverting input thereof at terminal 6 is connected from junction 161. The output terminal 7 of amplifier U16 is connected to junction 156. A resistor R54 is connected between junctions 161 and 163. A resistor R53 is connected between junctions 154 and 161. A resistor R48 is connected between junctions 159 and 160.

Transistors are provided at Q6, Q7, Q9 and Q10. Transistor Q9 has a base 166 connected from junction 156, a collector 167 connected from junction 153, and an emitter 168 connected to junction 155. Junctions 147, 154 and 155 are connected together. Transistor Q10 has a base 169, a collector 170 and an emitter 171. Emitter 171 is connected from junction 155. Base 169 is connected from junction 156. Collector 170 is connected to ground. Coil 12 is connected between junctions 147 and 149.

A resistor R43 is connected between junctions 153 and 157. Junctions 150 and 153 are connected together. A capacitor C23 is connected from junction 150 to ground.

A differential amplifier U15 has an inverting input terminal 2 and noninverting input terminal 3 and an output terminal 4. Output terminal 1 is connected to junction 152.

A capacitor C22 is connected from junction 158 to terminal 4 and to ground. Junction 158 is connected to junction 157 and to junction 162 from terminal 8 of amplifier U15. Terminal 2 of amplifier U15 is connected from junction 148. Terminal 3 of amplifier U15 is connected from junction 159.

Transistor Q6 has a base 172, a collector 174 and an emitter 175. Transistor Q7 has a base 173, a collector 176 and an emitter 177. Bases 172 and 173 are both connected from junction 152. Both emitters 175 and 177 are connected from junction 151. Junctions 149 and 151 are connected together. Collector 176 is grounded. Collector 174 is connected from junction 150. A resistor R44 is connected between junctions 148 and 149. A resistor R47 is connected between junctions 147 and 148.

OPERATION

As shown in FIG. 3, comparator 32 takes a somewhat sine wave type signal with some noise as indicated at 178 and converts it or squares it up as shown at 179.

Phase detector 20 shown in FIG. 3 takes an output signal of VCO 22 or a function thereof on lead 54 and compares it with the phase of the square wave 179. Integrator 19 is then driven thereby over lead 55 to lead 56 in FIG. 9 to cause the frequency and phase of VCO 22 to be appropriate to make the signal on lead 54 in FIG. 3 to be the same as that of square wave 179.

To make this function abundantly clear, phase detector 20 may act in the same manner as any conventional phase detector to drive integrator 19 and VCO 22 so that the same frequency and +90° phase different of the signal on input lead 54 are as those of the signal 179.

When actuated, integrator 19 shown in FIG. 4 presents a ramp or sawtooth on output lead 67 to cause VCO 22 to hunt for the phase and frequency of the incoming signal.

Integrator 19 in FIG. 4 has a lead 66 which is both an input and an output lead. It is an output lead because it is an output of amplifier U5. The same is impressed upon junction 112 in reset circuit 21 in FIG. 10, and the same is supplied to the noninverting input of amplifier U14 on terminal 5. Thus, when this exceeds the potential of junction 115, i.e., the potential of terminal 6 of amplifier U14, reset begins. Reset time is very short in comparison to the sweep time of integrator 19. At the end of the sweep, the FET Q3 is made conductive and the leads 65 and 66 are essentially shorted in both FIG. 10 and FIG. 4. This causes capacitor C12 in FIG. 4 to discharge and the sawtooth or ramp begins again.

Again, to make this function abundantly clear, the voltage on output lead 67 of integrator 19 shown in FIG. 4 is a more or less sawtooth voltage, the reset portion being essentially vertical while the ramp portion is at an angle with respect to the time axis which is substantially smaller than 90°.

Again, as the output of amplifier U5 in FIG. 4 seeks the right amplitude for the frequency of the incoming signal, the sweeping of the signal on lead 67 stops at an appropriate point directly proportional to the frequency of the incoming signal.

VCO 22 in FIG. 5 may be entirely conventional. Lead 67 in FIG. 4 is the input lead thereof in FIG. 5 and the frequencies on leads 23, 24 and 75 are all the same and are all directly proportional to the voltage on lead 67. The wave forms appearing on leads 23, 24 and 75 are indicated at 180, 181 and 182, respectively, in FIG. 5.

The synchronous detector 17 in FIG. 8 operates in the manner of a conventional synchronous detector. Synchronous detector 17 itself may be conventional.

In FIG. 8, a square wave may be impressed upon the gate of FET Q1 as indicated at 184. This ties terminal 5 of differential amplifier U12 to +7.5 volts when FET Q1 conducts. For a sine wave 185 on input lead 51, with square wave 184 of the same frequency and in synchronism therewith, the output lead 102 of synchronous detector 17 shown in FIG. 8 may be a full wave sine wave rectified shown at 183. When the full wave rectified signal 183 is produced, the same indicates that integrator 19 should look for the frequency of the incoming signal. Input lead 55 in threshold detector 18 in FIG. 9 is then connected directly via resistor 55 and an electronic switch Q4, which preferably takes the form of an FET, and lead 56 to the input of integrator 19. The same is accomplished because the average value of the full wave rectified signal 183 shown in FIGS. 8 and 9 is stored in capacitor C4 in FIG. 8, and the same raises the potential of lead 102 in FIG. 9 to cause differential amplifier U13 to turn on transistor Q11 to back bias and FET Q2. As stated previously, this then allows electronic switch Q4 to connect leads 55 and 56 in FIG. 9. Integrator 19 is then caused to track the incoming signal via the VCO 22.

As stated previously, the bridge driver 15 in FIG. 13 may be conventional. The conventional probe 11 shown in FIG. 1 vibrates vane 13 through a magnetostrictive driver. It is the current in coil 12 in FIG. 13 that determines the nature of the magnetostriction. The bridge driver 15 thus keeps the current in coil 12 as indicated at 186 in FIG. 13.

Driver coil 12 in probe 11 vibrates vane 13. Piezoelectric crystal 14 is fixed relative to vane 13 and therefore produces an alternating output voltage which is impressed upon preamplifier 16. Preamplifier 16 provides inputs to synchronous detector 17 and comparator 32. Synchronous detector 17 produces the full wave sine wave rectified signal 183 shown in FIGS. 8 and 9. This is impressed upon threshold detector 18 which detects the synchronization of square wave 184 and input signal 185 in FIG. 8, both in frequency and 180 degree out of phase. Responsive to this, threshold detector 18 connects phase detector 20 to integrator 19. Prior thereto reset circuit 21 in FIGS. 9 and 10 and shown at 21 in FIG. 1 cause the integrator 19 to produce a sawtooth to operate VCO 22.

When VCO 22 follows the frequency of the output of crystal 14 in FIG. 1, the output of inverter 28 will have a signal of a period T such that $$d = AT^2 + B$$

where d is the density of the fluid in which probe 11 is immersed, and A and B are empirical constant determined in the conventional way.

Figure 14:
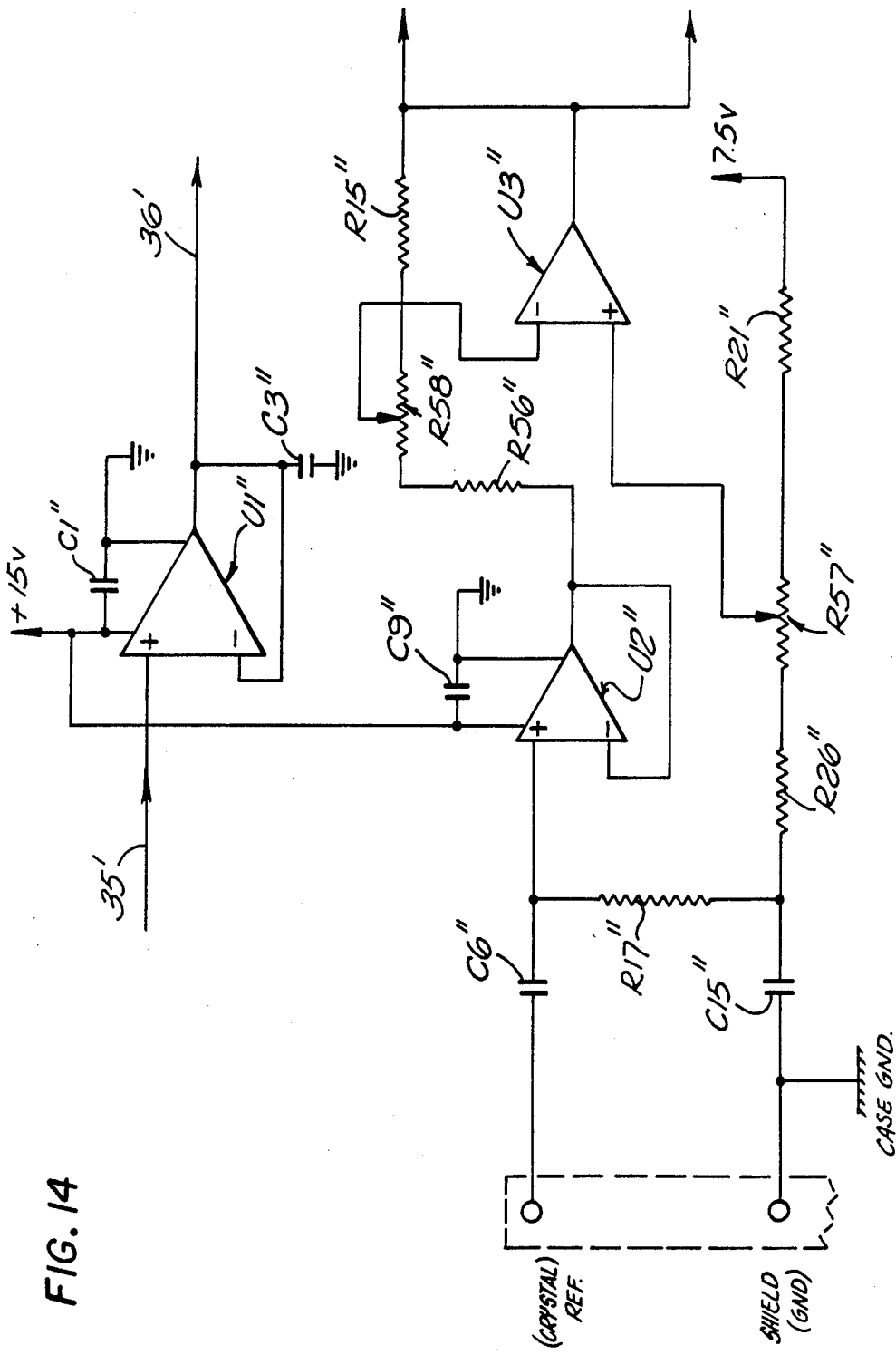
FIG. 14 is a schematic diagram of an alternative preamplifier.

There are at least two possible preamplifier circuitries. The one disclosed in FIG. 2 will be used for an ungrounded crystal (isolated from the case) and preamplifier 16' shown in FIG. 14 will be used for a single wire crystal output where one end of the crystal is mounted directly to the case and provides electrical continuity to the case. The single wire crystal output will appear in our present design.

A lock-unlock hysteresis is a feature of detector circuit 18 of FIG. 9 which can be set by R3 of new FIG. 9.

Circuit values may be as follows:

| Amplifier | U1 | TL062I |
| Amplifier | U2 | TL062I |
| Amplifier | U3 | TL062I |
| Comparator | U4 | LM2901N |
| Amplifier | U5 | TL062I |
| Comparator | U11 | LM2901N |
| Amplifier | U12 | TL062I |
| Comparator | U13 | LM2901N |
| Amplifier | U14 | TL062I |
| Amplifier | U15 | TL062I |
| Amplifier | U16 | TL062I |
| Capacitor | C1 | .01 µf/100 volts |
| Capacitor | C2 | .01 µf/100 volts |
| Capacitor | C2 | .01 µf/50 volts |
| Capacitor | C3 | 1 µf/50 volts |
| Capacitor | C4 | 1 µf/25 volts |
| Capacitor | C5 | .1 µf/100 volts |
| Capacitor | C6 | .01 µf/100 volts |
| Capacitor | C7 | 470 pf/200 volts |
| Capacitor | C8 | 1 µf/50 volts |
| Capacitor | C9 | .01 µf/100 volts |
| Capacitor | C10 | 100 pf/200 volts |
| Capacitor | C11 | .1 µf/100 volts |
| Capacitor | C12 | 1 µf/100 volts |
| Capacitor | C13 | 4.7 µf/35 volts |
| Capacitor | C14 | .1 µf/100 volts |
| Capacitor | C15 | 4.7 µf/35 volts |
| Capacitor | C16 | .01 µf/100 volts |
| Capacitor | C17 | .01 µf/100 volts |
| Capacitor | C18 | .01 µf/100 volts |
| Capacitor | C20 | 1 µf/50 volts |
| Capacitor | C21 | .47 µf/50 volts |
| Capacitor | C24 | 100 pf |
| Capacitor | C25 | 1 µf/50 volts |
| Comparator | U8 | LM2901N |
| Component | TS1 | V36ZA80 |
| Component | TS2 | V12ZA1 |
| Component | TS3 | V18ZA3 |
| FET | Q1 | J113 |
| FET | Q2 | J113 |
| FET | Q3 | J113 |
| FET | Q4 | J113 |
| Gate | U7 | MC1407 |
| Gate | U9 | MC1407 |
| Gate | U10 | MC1407 |
| Phase Detector | U5' | MC1407 |
| Potentiometer | R40 | 20 K |
| Resistor | R1 | 100 K |
| Resistor | R3 | 10 K |
| Resistor | R4 | 95.3 K |
| Resistor | R5 | 10 K |
| Resistor | R7 | 100 K |
| Resistor | R8 | 10 K |
| Resistor | R9 | 10 K |
| Resistor | R10 | 49.9 K |
| Resistor | R11 | 100 K |
| Resistor | R12 | 10 K |
| Resistor | R13 | 10 K |
| Resistor | R14 | 100 K |
| Resistor | R16 | 7.5 K |
| Resistor | R17 | 1 M |
| Resistor | R18 | 49.9 K |
| Resistor | R19 | 49.9 K |
| Resistor | R20 | 180 ohms |
| Resistor | R21 | 510 K |
| Resistor | R22 | 10 K |
| Resistor | R24 | 1.5 M |
| Resistor | R25 | 100 K |
| Resistor | R26 | 1 K |
| Resistor | R27 | 23.7 K |
| Resistor | R28 | 100 K |
| Resistor | R29 | 10 K |
| Resistor | R30 | 10 K |
| Resistor | R31 | 100 K |
| Resistor | R33 | 2.7 K |
| Resistor | R34 | 10 K |
| Resistor | R36 | 33 ohms (1 watt) |
| Resistor | R37 | 10 K |
| Resistor | R39 | 20 K |
| Resistor | R40 | 28 K NOM. |
| Resistor | R41 | 10 K |
| Resistor | R42 | 10 K |
| Resistor | R43 | 390 ohms (1 watt) |
| Resistor | R44 | 10 K |

-continued

| | | |
|---|---|---|
| Resistor | R45 | 10 K |
| Resistor | R46 | 4.99 K |
| Resistor | R47 | 10 K |
| Resistor | R48 | 82 K |
| Resistor | R49 | 7.15 K |
| Resistor | R50 | 2.8 K |
| Resistor | R51 | 10 K |
| Resistor | R52 | 200 ohms (¼watt) |
| Resistor | R53 | 49.9 K |
| Resistor | R55 | 100 K |
| Resistor | R56 | 3.81 K NOM (S.A.T.) |
| Resistor | R57 | 49.9 K |
| Resistor | R59 | 23.7 K |
| Resistor | R60 | 100 K |
| Transistor | Q2 | J113 |
| Transistor | Q4 | J113 |
| Transistor | Q5 | 2N3904 |
| Transistor | Q6 | 2N3904 |
| Transistor | Q7 | 2N3906 |
| Transistor | Q8 | 2N2905 |
| Transistor | Q9 | 2N3904 |
| Transistor | Q10 | 2N3906 |
| Transistor | Q11 | 2N3906 |
| VCO | U6 | ICL8038 |
| Voltage Regulator | VR1 | 78M15 |

FIG. 14

| | | |
|---|---|---|
| Amplifier | U1″ | TL062I |
| Amplifier | U2″ | TL062I |
| Amplifier | U3″ | TL062I |
| Capacitor | C1″ | .01 µf/50 volts |
| Capacitor | C3″ | 1 µf/35 volts |
| Capacitor | C6″ | .01 µf/50 volts |
| Capacitor | C9″ | .01 µf/50 volts |
| Capacitor | C15″ | 4.7 µf/35 volts |
| Resistor | R15″ | 49.9 K |
| Resistor | R17″ | 10 M |
| Resistor | R21″ | 499 K |
| Resistor | R26″ | 100 K |
| Resistor | R56″ | 10 K |
| Resistor | R57″ | 200 K ADJ (4 turn) |
| Resistor | R58″ | 20 K GAIN ADJ (4 turn) |

What is claimed is:

1. A vibration densitometer comprising: a probe; a vibratable vane supported in said probe; electromagnetic means to cause said vane to vibrate; a sensor to produce an alternating electrical output signal of a frequency which is a function of the density d of the fluid surrounding said probe; a preamplifier connected from said sensor; a synchronous detector connected from said preamplifier; a phase detector having first and second inputs, said first input being connected from said preamplifier; an integrator, said phase detector having an output; an electronic switch connected from said phase detector output to said integrator; a threshold detector connected from said synchronous detector to said electronic switch; a voltage controlled oscillator (VCO) having an input connected from said integrator; first output means; a phase shifter connected from said first output means to said synchronous detector; a driver connected from said VCO to said electromagnetic means; a buffer having an input connected from said first output means and an output; and second output means responsive to the output of said buffer for producing a signal of a magnitude directly proportional to the said density d, where $d = AT^2 + B$, A is a constant, B is a constant, T is the period of the output signal of said buffer.

2. The invention as defined in claim 1, wherein a reset circuit is connected across said integrator.

3. The invention as defined in claim 2, wherein said phase detector includes a first exclusive OR gate.

4. The invention as defined in claim 3, wherein said first output means includes first, second and third output leads carrying a square wave, a triangle wave and a sine wave thereon, respectively, said waves being of the same period and synchronous with each other, a comparator having an inverting input connected from said second lead, a second exclusive OR gate, said comparator having an output connected to a positive potential source via a first resistor, said second exclusive OR gate having one input from said first lead and a second input from a positive potential source, a second resistor connected from the output of said second exclusive OR gate having one input from said first lead and a second input from a positive potential source, a second resistor connected from the output of said second exclusive OR gate to the noninverting input of said comparator, the output of said second exclusive OR gate being connected to said phase shifter input and to said second input of said phase detector, a third exclusive OR gate having one input connected from said first lead and another input connected to a potential source, the output of said third exclusive OR gate being connected to said buffer, said third lead being connected to said driver.

* * * * *